United States Patent [19]

Liston et al.

[11] Patent Number: 4,595,562
[45] Date of Patent: Jun. 17, 1986

[54] LOADING AND TRANSFER ASSEMBLY FOR CHEMICAL ANALYZER

[75] Inventors: Max D. Liston, Irvine; Paul K. Hsei, Huntington Beach, both of Calif.

[73] Assignee: American Hospital Supply Corporation, Evanston, Ill.

[21] Appl. No.: 551,437

[22] Filed: Nov. 14, 1983

Related U.S. Application Data

[63] Continuation of Ser. No. 284,840, Jul. 20, 1981, abandoned.

[51] Int. Cl.$^4$ .................. G01N 35/04; G01N 35/06
[52] U.S. Cl. .................. 422/65; 198/465.1; 414/417; 422/63; 422/64; 422/102; 422/67
[58] Field of Search .................. 422/63–67, 422/100, 102; 414/417; 198/472; 364/447, 448; 356/246, 435, 436

[56] References Cited

U.S. PATENT DOCUMENTS

| | | | |
|---|---|---|---|
| 3,504,376 | 3/1970 | Bednar et al. | 422/67 |
| 3,544,272 | 12/1970 | Vaills | 422/65 |
| 3,589,867 | 6/1971 | Heinz et al. | 423/230 R |
| 3,754,872 | 8/1973 | Zauft | 422/63 |
| 3,770,382 | 11/1973 | Carter et al. | 422/65 |
| 3,917,455 | 11/1975 | Bak et al. | 422/65 |
| 4,058,367 | 11/1977 | Gilford | 422/63 |
| 4,113,436 | 9/1978 | Werder | 422/67 |
| 4,224,032 | 9/1980 | Glover et al. | 422/65 |
| 4,228,831 | 10/1980 | Kerns | 422/100 |
| 4,234,540 | 11/1980 | Ginsberg et al. | 422/64 |
| 4,325,909 | 4/1982 | Coulter et al. | 422/100 |
| 4,338,279 | 6/1982 | Orimo et al. | 422/65 |

FOREIGN PATENT DOCUMENTS

| | | | |
|---|---|---|---|
| 55-1551 | 1/1980 | Japan | 422/67 |
| 55-140154 | 11/1980 | Japan | 422/64 |

Primary Examiner—Michael S. Marcus
Attorney, Agent, or Firm—John H. Faro

[57] ABSTRACT

The present invention relates to an assembly and method for introducing and transporting sample containers in a chemical analyzer, and in particular, to an assembly for organizing randomly loaded sample containers in a positively-identifiable fashion. The assembly additionally includes a means for sequencing the organization of sample containers and a novel means for dispensing measured amounts of sample therefrom.

1 Claim, 16 Drawing Figures

LOADING AND TRANSFER ASSEMBLY FOR CHEMICAL ANALYZER

This application is a continuation of application Ser. No. 284,840 filed July 20, 1981 now abandoned.

BACKGROUND OF THE INVENTION

Biological fluids are routinely analyzed in hospital clinical laboratories to aid in the diagnosis of disease and to provide critical information about a patient's well being. The constituents of blood, lymph, urine or products derived therefrom provide meaningful information to a clinician about his or her patient's health. With physicians becoming increasingly dependent on clinical laboratory data for the diagnosis of disease and the monitoring of therapy, automation has become essential to processing the increasing workload in hospital clinical laboratories. Automated chemical analysis of biological fluid constituents has solved a great number of problems associated with conducting reliable and efficient analysis; it has, at the same time, however, has created its own dilemmas. Two logical alternatives to automation are either a much larger laboratory staff or much more judicial selection of appropriate laboratory tests by physicians. Since neither of these solutions is practical, however, the trend is toward advanced automated chemical analyzers that meet the needs of the present day analyst. Although automation provides a means by which an increased workload can be processed rapidly and reproducibly, limitations in the design of automated instruments make it difficult to achieve error free results of acceptable quality.

In clinical chemistry, the term "automation" implies the performance of analytical tests through mechanical or electronic control by an instrument with only minor involvement of an analyst. In the same context, partial automation refers to procedures in which the initial preparation of a specimen is done manually, but in which the analysis proceeds without human intervention. Presently, the vast majority of chemical analyzers require considerable manipulations by laboratory technicians and thus fall into the latter category. Illustrative of these are the allocation of a patient's fluid specimen for various types of analyses conducted either manually or in various instruments; appropriate dilution of specimen to meet the requirements of the various procedures; and complex book-keeping in order to keep track of the disposition and concentrating of the patient's specimen being analysed. On the other hand, totally manual analysis is also performed for specific tests not amenable to automated procedures, or where automated systems are either too expensive or cannot adequately be maintained. Since increased efficiency and reliability are necessary in the clinical laboratory, it is generally desirable to perform as many steps as possible without this manual intervention. Full automation reduces the possibility of human errors that arise from technicians making repetitive and boring manipulations, such as identifying, pipetting and analyzing a multitude of specimens.

Reliability and reproducibility of automated analytical test results in a clinical chemistry laboratory are essential to maintaining the accuracy of meaningful results to the clinician. Basically, the accuracy provided by automated chemical analyzers is no better than that obtained by carefully conducted conventional techniques; however, the precision (repeatability) is greatly increased. Measurement repeatability is often poor when manual analysis is employed as a consequence of some bias introduced into the analysis by an individual technologist. Furthermore, the ideal automated analytical system should employ the rapidity and simplicity of operation necessary for emergency "stat" tests, small volume specimens required for pediatric patients, and the high throughput required for routine analysis. Automated equipment that is properly designed offers greater reliability, less operative bias and more rapid evaluation of patient samples than is possible with manual methods.

Whether analysis is performed manually, automatically or uses a combination of the two, the basic steps common to the analysis cycle are: sample entry into the instrument, sample distribution with or without subsequent washout of the sample probe, reaction of sample with one or more reagents, followed by a quantitative determination of sample parameters and data presentation. Major drawbacks of currently used automated or partially automated chemical analyzers include: the need of highly trained laboratory personnel for the entry of sample and the operation of the instruments; specimen contamination and variability of results due to carry-over from adjacent specimens; a low throughput of samples to be analyzed; the lack of versatility to conduct many tests on the same specimen while retaining the capability of performing the same test on a multitude of different specimens in a short period of time; and the absence of satisfactory back-up or control systems to conveniently ensure the veracity of test results, and lack of positive sample identification. The lack of positive sample identification in a clinical chemistry laboratory is crucial since the miscorrelation of tests results with a patient's specimen can lead to incorrect diagnosis and consequently deprive the patient of proper therapy. Extensive manipulation of a patient's specimen considerably increases the chances of incorrectly assigning the wrong test results to that specimen. Although several automated instruments have addressed the problem of positive sample identification, none have adequately solved it.

Heretofore, automatic chemical analyzers have suffered from some or all of these problems and thus have not provided the clinician with the reliability and versatility necessary for the operation of modern clinical laboratories.

SUMMARY OF THE INVENTION

The present invention avoids the above-noted problems and drawbacks found with conventional chemical analyzers by providing a loading and transfer assembly for presenting containers having fluid samples therein to a chemical analyzer which performs selected tests on the fluid samples. The assembly comprises a loading means for retaining the sample containers that have been randomly positioned therein; a first means associated with said loading for sequentially removing said sample containers positioned therein; a transfer means for receiving said sample containers removed from said loading means; a means associated with said transfer means for dispensing a least a portion of the fluid sample in each said sample container into the chemical analyzer; a second means associated with said transfer means for sequentially removing said sample containers received therein; a storage means for receiving said sample containers removed from said transfer means; and a logic means for sequencing the operation of said loading, first removing, transfer, identifying, dispensing, second removing and storage means in response to the operation of said chemical analyzer and for positively associating the test result obtained with a particular fluid sample in the chemical analyzer with the identification obtained by said identifying means from the sample container from which said fluid sample was dispensed.

DETAILED DESCRIPTION OF THE PREFERRED EMBODIMENT

The loading and transfer assembly of the present invention is a universal system which can be adapted for use with any automated chemical analyzer requiring acquisition of sample for analysis. Of the three major types of automated chemical analyzers presently available (the continuous-flow, discrete-sample and centrifugal force analyzers), the discrete-sample processing analyzer is preferred in accordance with the present application.

Figure 1:
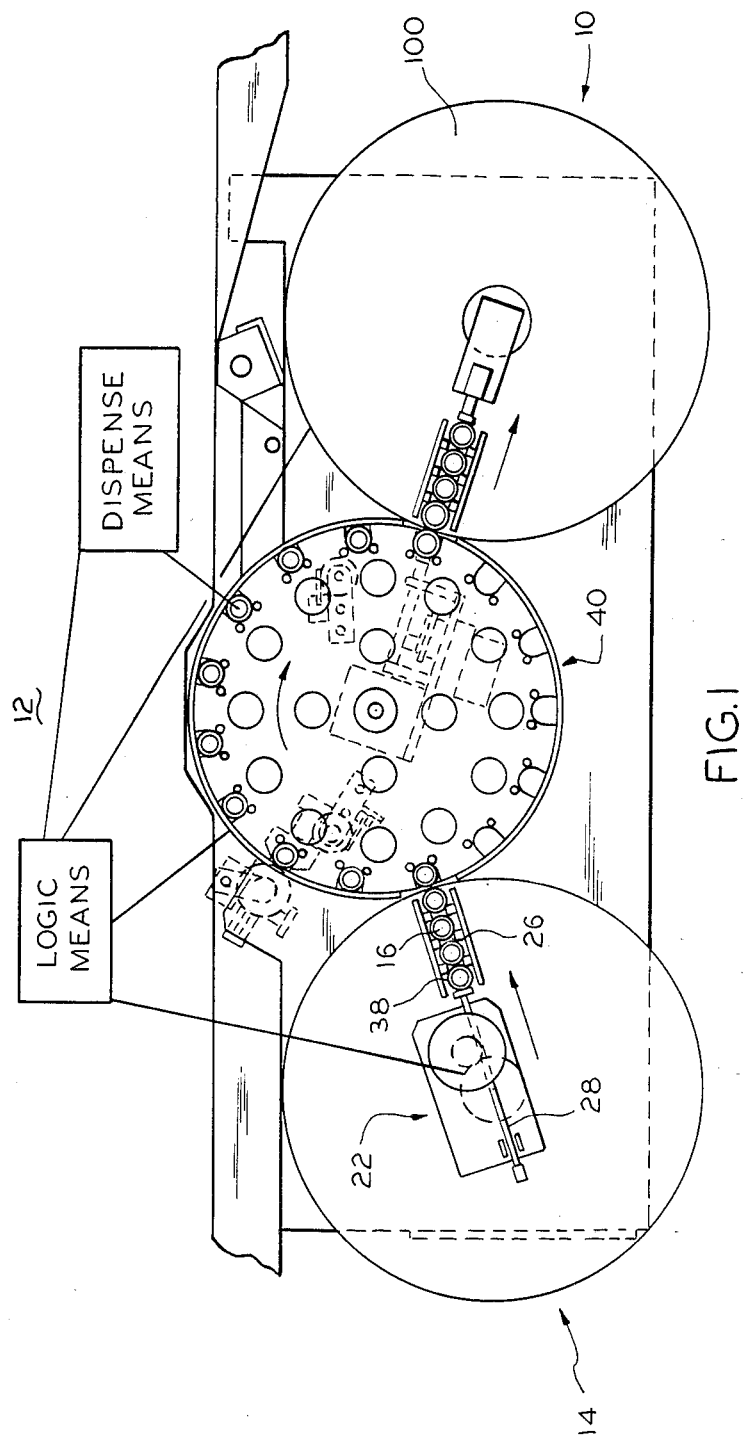
FIG. 1 is a top view of the preferred loading and transport assembly of the present invention.
Figure 2:
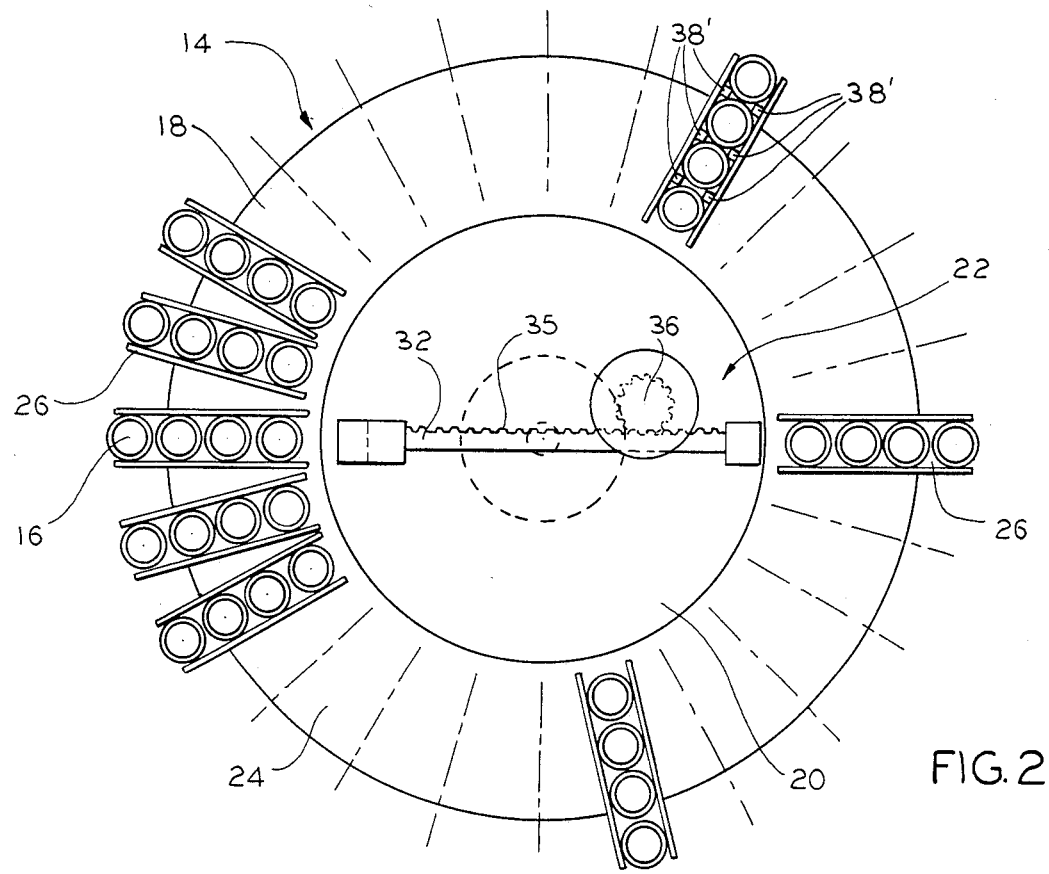
FIG. 2 is a top partial view of the loading carousel having a number of sample containers loaded therein.
Figure 3:
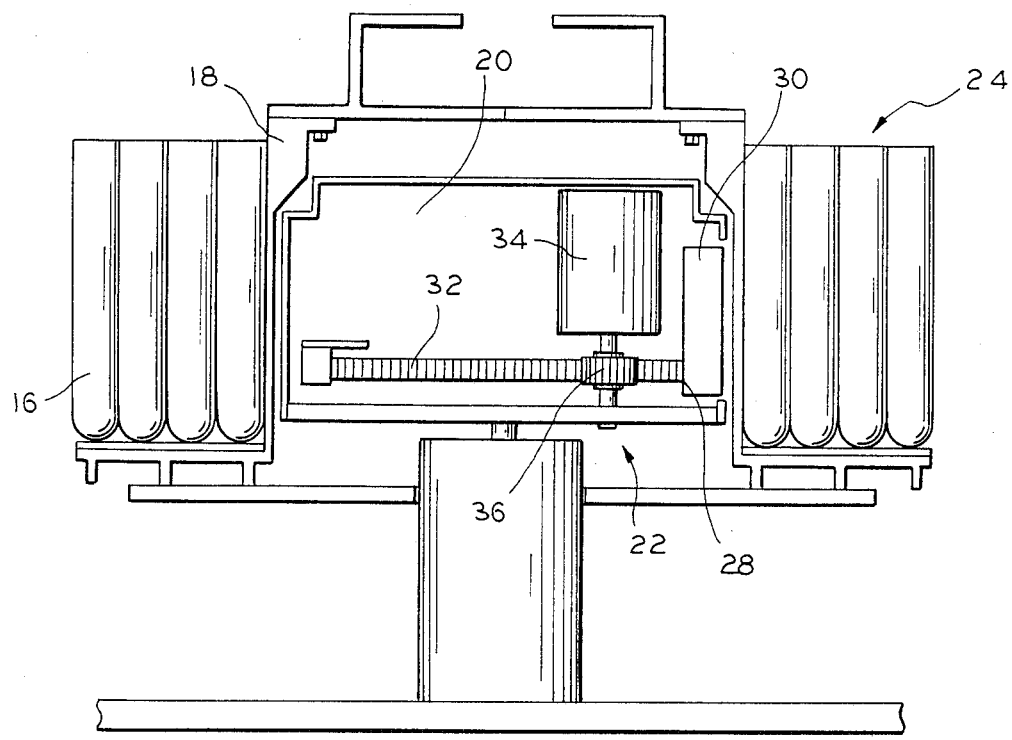
FIG. 3 is a front elevated view, of a semi-circular loading carousel mounted in the assembly in accordance with one embodiment of the present invention.
Figure 4:
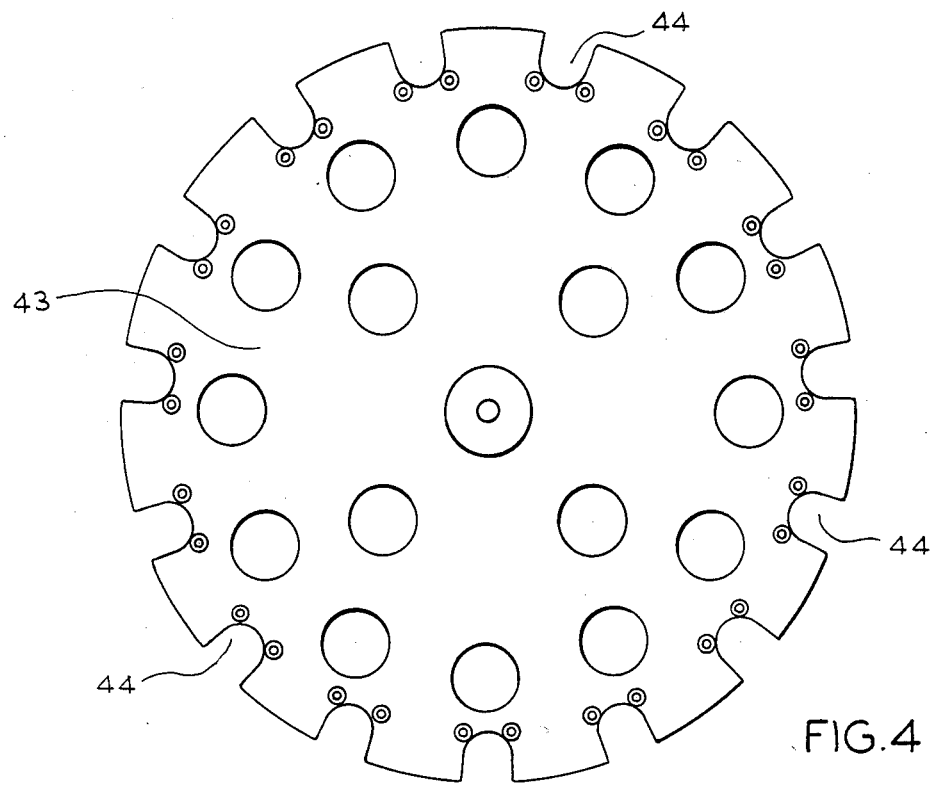
FIG. 4 is a top view of the upper portion of the transfer carousel in accordance with the present invention.

A loading and transfer assembly, in accordance with the present invention, is generally shown in FIG. 1 at 10 to depict the relationship between the assembly and the chemical analyzer 12. The assembly 10 first includes a loading means 14 for retaining a number of sample containers 16 that have been randomly loaded therein by a laboratory technician or physician. Prior to loading of the sample container in the loading means 14, no manipulation is required other than centrifugation of a patient's clotted blood to produce serum and the application of an identification label as described in detail below. The sample container loading means of the present invention is preferably a rotating carousel 18 as shown in FIG. 2 and 3 having a substantially hollow inner core portion 20 large enough to house a mechanism 22 for displacing the sample containers therefrom. The peripheral portion 24 of the carousel has a plurality at radially extending slots 26 for receiving a number of conventional blood collection containers 16. The carousel 18 is removably mounted in the assembly and thus allows the analyst to load sample containers individually therein, prior to placing the carousel in position. This collective loading is advantageous to the analyst because it reduces the error associated with entry by decreasing the manipulation by the analyst.

In the most preferred embodiment of the present invention, the loading carousel 18 is constructed of two semi-circular carousel portions, each having twelve radially extending slots 26 large enough to hold four sample containers 16 each. The assembly 10 thus has the capability of continually supplying sample containers to the instrument for analysis, since each semi-circular component of the carousel 18 can be individually mounted or removed without interrupting the subsequent transfer process as described hereinafter. This allows the hospital clinician to efficiently conduct analyses on numerous samples and to provide test results on a continuous basis.

In one embodiment of the present invention, as shown in FIGS. 2 and 3, the loading carousel 18 is doughnut-shaped, having a hollow inner core 20 and a peripheral portion 24 constructed for receiving the sample containers. The inner core 20 is large enough to house a sample container displacing mechanism generally shown at 22 which laterally displaces the sample containers from the radially extending slots 26. One such means for displacing the sample containers from the loading carousel 18 includes a horizontal pushing arm 28 having a vertical member 30 for abutment against the containers and a horizontal member 32 connected thereto which engages a motor 34 to laterally displace the horizontal member 32. Upon activation of the motor, the projections 35 in the horizontal 32 member are engaged by a gear 36 thus transmitting a force to the sample containers 16 and sequentially displacing them from the carousel 16.

In the preferred embodiment of the present invention, the pushing arm 28 is operated under tension. The tension pushing arm 28 maintains the sample containers in a vertical position at all times during displacement from the carousel so that jamming of the containers between the loading and transfer carousels is avoided. In accordance with the present invention, the pushing arm 28 is constructed such that it is capable of disengaging the motor from the horizontal member 32 when the laterally displaced container encounters resistance from the transfer carousel as described in detail below. Intermittent engagement of the motor 34 with the horizontal member 32 insures the constant tension required to maintain the vertical position of the containers, while at the same time preventing the containers from being broken.

The radially extending slots 26 in the carousel 18 are equipped with constricted segments 38 or 38' which engage the outer walls of the sample containers and retain the containers in a fixed position. In this way, the sample containers are prevented from shifting position within the slot 26, or falling out of the carousel 18 unless displaced during the normal operation of the analyzer.

Conventional blood collection tubes such as VACU-TAINERS* (*Registered Trademark of Becton-Dickinson) or specially constructed microcontainers can be used in accordance with the present invention as further described below.

The transfer means of the present invention generally shown at 40, is a crucial component of the entire assembly and functions as a mediator between the loading of samples into the chemical analyzer, the identification of samples and consequent recognition of tests to be performed, dispensing of samples from the containers and, finally, dispensing of the sample containers from the transfer means 40 to a storage means retaining them in an organized and positively identified manner. The preferred transfer means, in accordance with the present invention, is a rotating carousel 42 having an upper portion 43 with a plurality of semicircular slots 44 circumscribed around its periphery for receiving and retaining samples from the loading carousel 18. The size and shape of the slots 44 coincide generally with the dimensions of the sample container to be placed therein. The loading 18 and transfer 42 carousels are preferably positioned adjacent to each other such that direct exchange of sample containers 16 from the loading carousel 18 is facilitated and cumbersome conveyor assemblies can be eliminated. Preferably, the loading and transfer carousels are mounted for rotation about their respective axes in opposite directions. In one embodiment of the present invention, the loading carousel 18 is mounted for counter clockwise rotation and the transfer carousel 42 is mounted for clockwise rotation.

The transfer carousel 42 includes many features which assist in the identification and dispensing of sample from the containers, said features capable of being used alone or in combination with each other as described herein. Many of these features are amenable to variations in structural design, and therefore are described herein as the preferred embodiments in accordance with the present invention.

Figure 5:
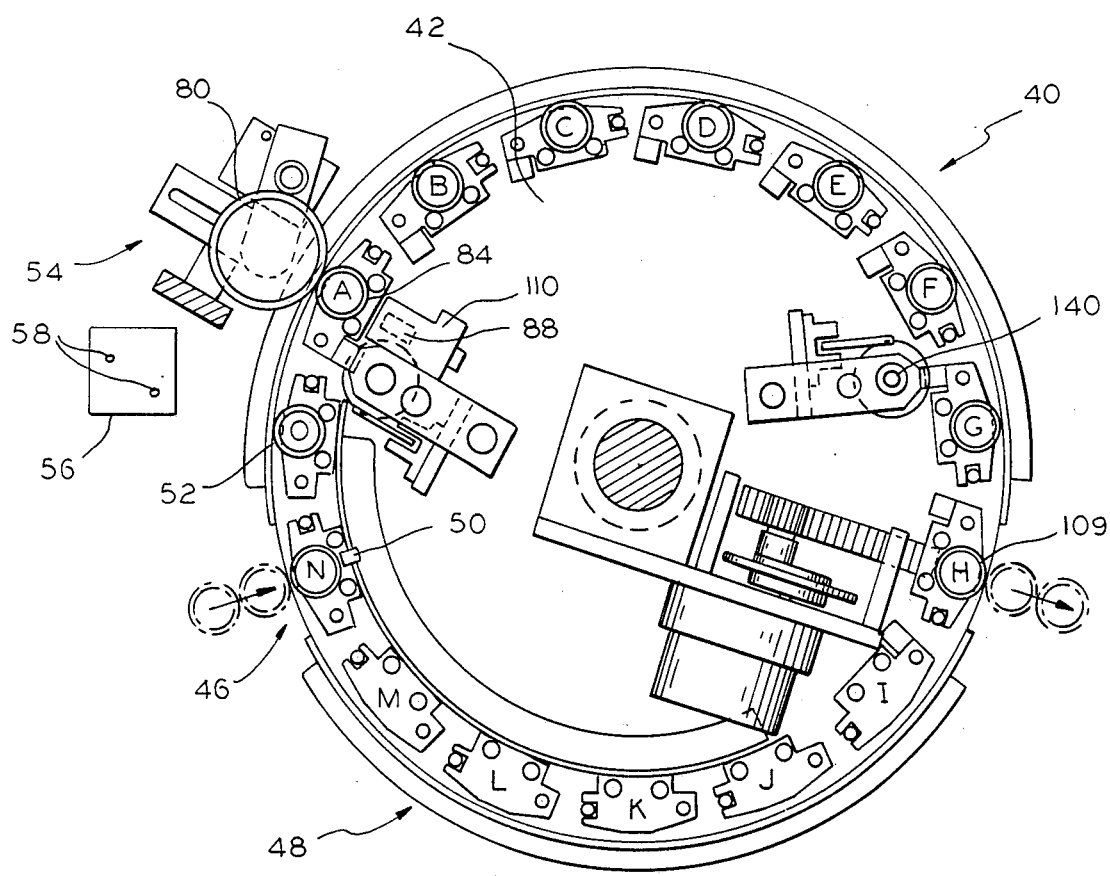
FIG. 5 is a top view, of the transfer carousel having the upper portion removed therefrom.
Figure 15:
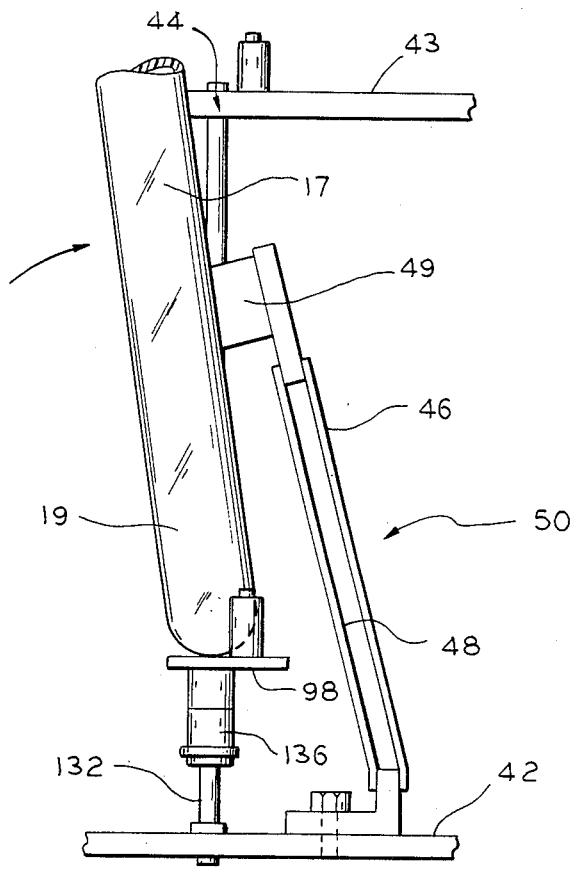
FIG. 15 is a side elevational view of the container receiving position and related apparatus of the transfer assembly in accordance with the present invention.
Figure 16:
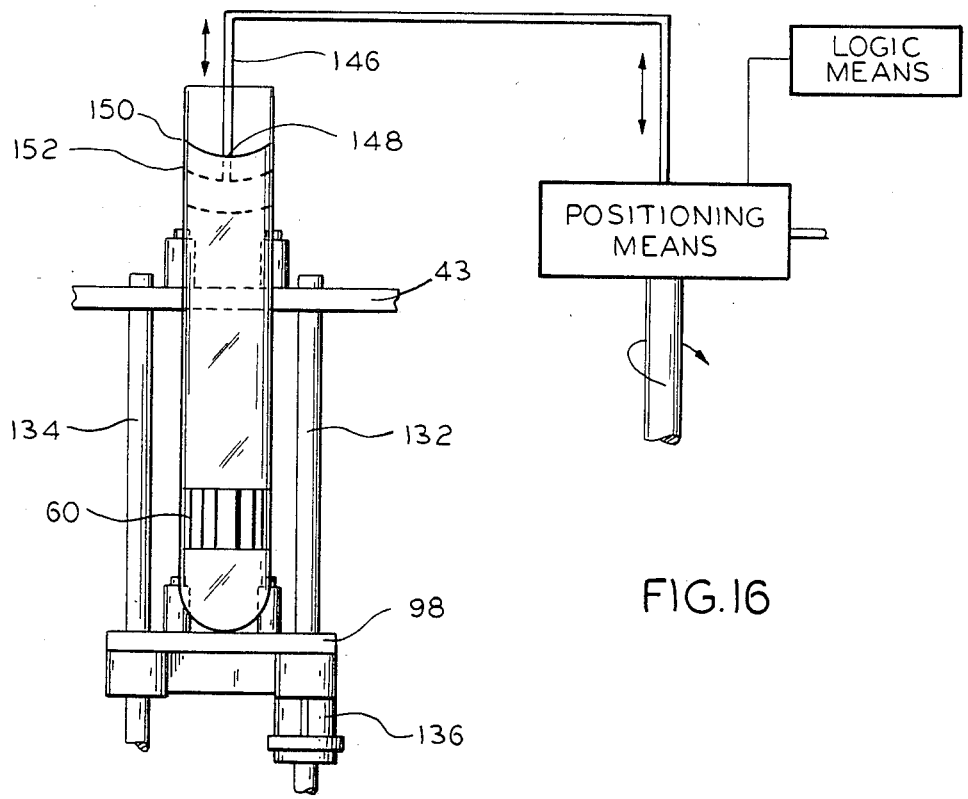
FIG. 16 is a front elevational view of the sample dispensor in accordance with, the present invention.

As shown in FIGS. 5 and 15 the first component of the transfer carousel includes a means 46 for preventing the harsh (non-gentle) transfer of the sample containers into the carousel 42. As the containers are displaced from the loading carousel 18, the top portion of the container 17 is generally at a position behind the bottom portion as the container enters the transfer slot 44 associated with the container exchange position 50. As the bottom portion 19 of the container meets resistance from the transfer carousel, the upper portion 17 snaps into position against the upper portion 43 of the carousel, resulting in spillage of fluid and cracking of glass containers. An anti-splash 46 device prevents sample from splashing out of the containers as they are transferred into the transfer carousel 42, and will also prevent cracking of glass containers. The anti-splash device 46 of the present invention is preferably a spring-tension arm 48 which is obliquely mounted on the bottom of the carousel 42 as shown in FIG. 15. Disposed at the top portion of the arm 48 is a contact member 49 positioned to contact the containers during exchange. The spring-tension arm cushions the entry of the upper portion of the container as it is transferred.

The second component of the transfer carousel 42 is a means for randomly introducing sample containers into the assembly 10 forward of the pre-loaded containers. This usually occurs when a patient's specimen must be analyzed on emergency basis, and is generally known as a "stat" situation. In accordance with the present invention, the transfer carousel 42 is equipped with a means for randomly introducing emergency or "stat" specimens forward of the pre-loaded containers while maintaining the original position of those containers in the assembly. There are two "stat" loading positions in accordance with the present invention. The first "stat" loading position 48 is generally shown in FIG. 5 as including sample container retaining slots I, J, K, L, and M. These "stat" loading positions precede the fixed sample exchange slot position 50 (N) in the clockwise rotational cycle of the carousel. Introduction of "stat" samples into these carousel positions insures the maintenance of the pre-loaded sample container positions in both the loading 18 and transfer 42 carousels.

The second "stat" loading position 52 (O) is located immediately forward of said exchange position 50 and directly rearward of a sample identifying means 54 having tube in position (A). Unless this "stat" loading position (O) is empty, a pre-loaded container must be removed from the assembly before the "stat" specimen is introduced. Since both "stat" loading positions precede the identifying means 54 in the rotational cycle of the assembly, random loading of the "stat" specimens is facilitated and the positive sample identification feature of the present invention is not precluded.

A signaling means 56 is associated with the transfer carousel and is preferably located adjacent to the second "stat" position 52. The signaling means warns the analyst when the carousel 42 is ready to advance a step in its rotational cycle. Thus, when the analyst is required to load one or more "stat" samples into the transfer carousel, he or she is provided with a means for doing so safely. A pair of light-emitting diodes 58 are associated with the signaling means 56 as indicators of the rotational status of the carousel 42. Illustrative of this is the stand-by mode wherein one of the light-emitting diodes illuminates a red color and the rotational mode wherein the other diode illuminates a green color. The clinician can safely place a sample container in the stat position at 52 (O) of the transfer carousel only in the stand-by mode.

The third component of the transfer carousel 42 is a means for positively identifying sample containers in the carousel, and for obtaining specific instructions for the chemical analysis of the sample within the assembly of the present invention such that the location of sample container is positively identified. Up to this point, the patient's specimen has been randomly loaded within the analyser assembly 10 and has thus required no error-prone and time-consuming record keeping procedures. This is a major advantage of the present invention over the prior art since it eliminates sources of error, saves precious time and allows the clinician to conduct significantly more analyses than he or she could do otherwise.

Figure 9:
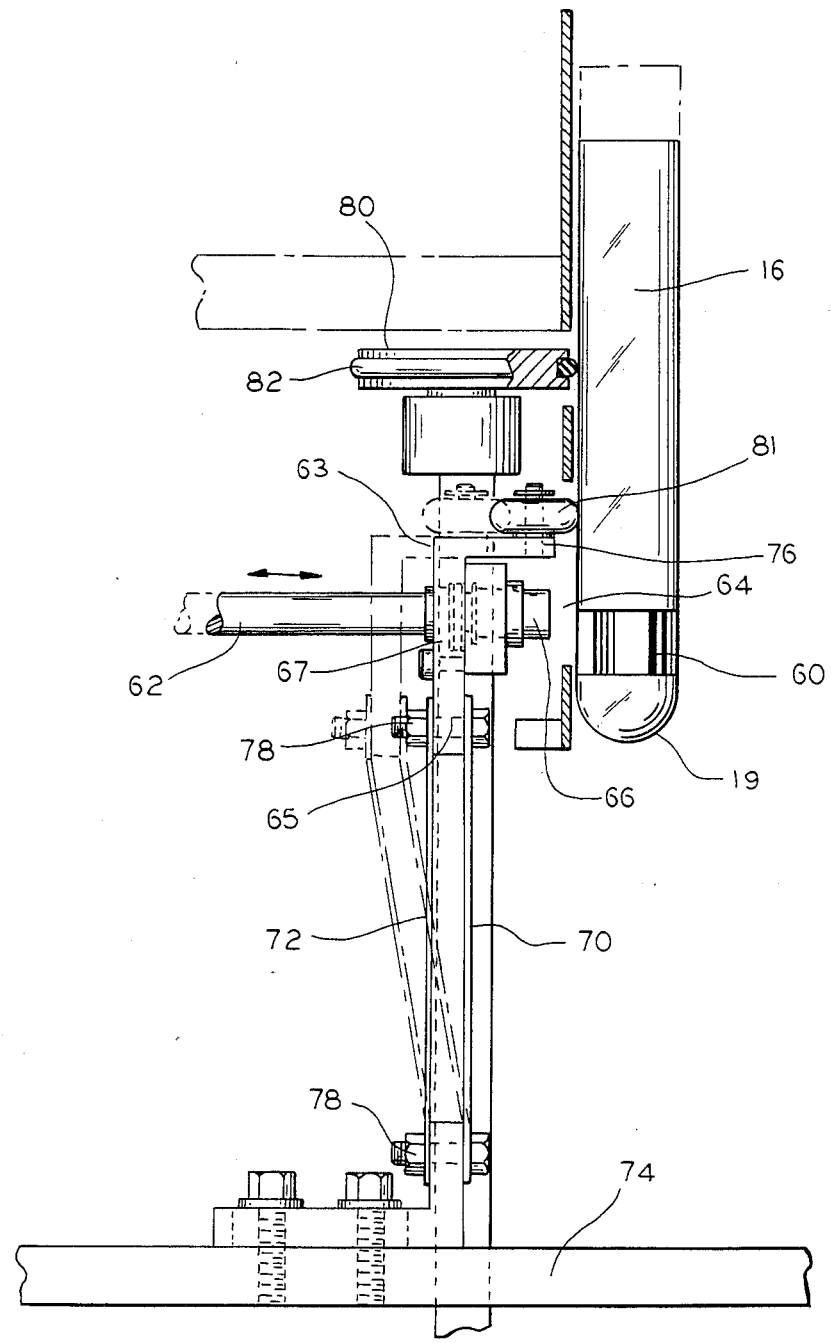
FIG. 9 is a side view of the bar code sensor, rotational means, and means associated with said bar code sensor for maintaining its fixed position in accordance with one embodiment of the present invention.
Figure 10:
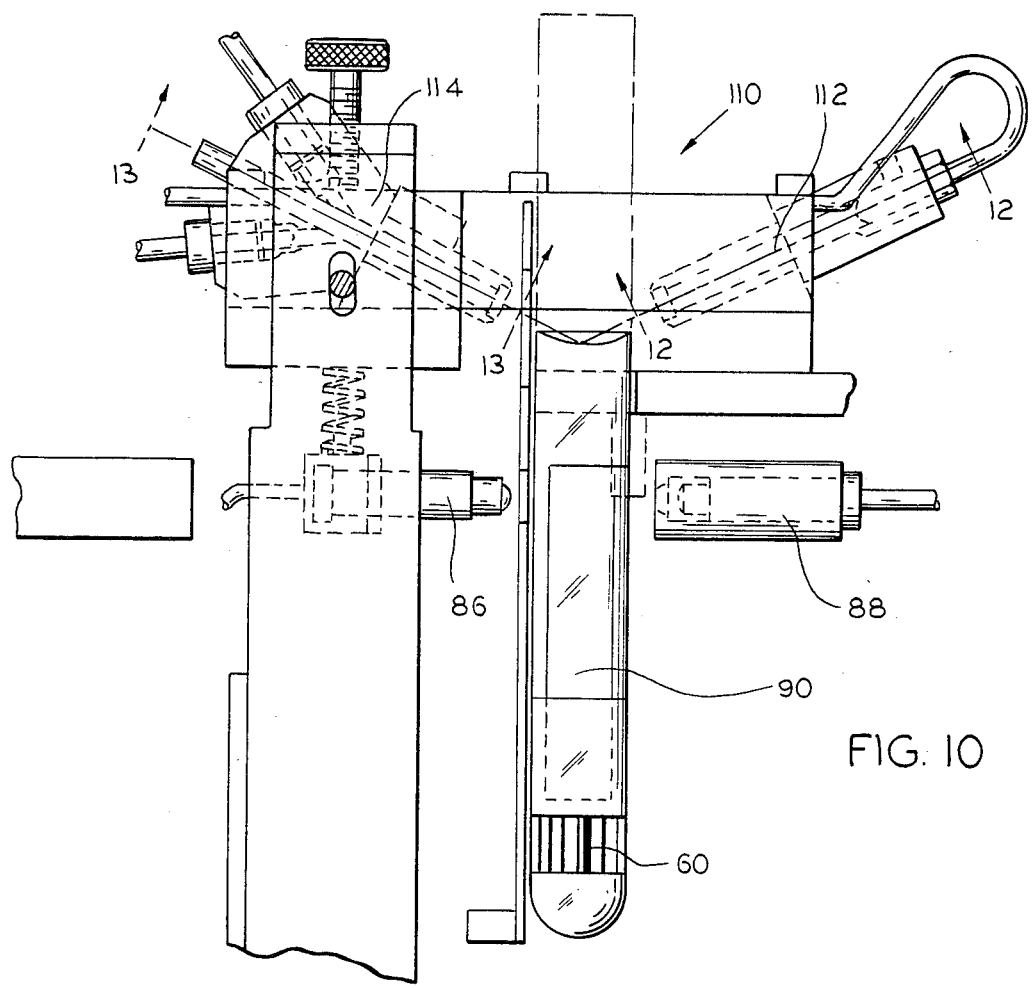
FIG. 10 is a side view of the fluid level detection system in accordance with one embodiment of the present invention.
Figure 11:
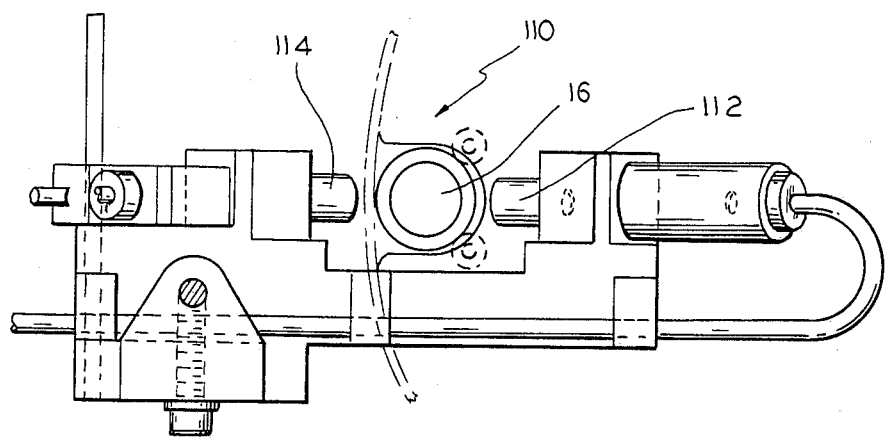
FIG. 11 is a top view of the fluid level detection system of the present invention.
Figure 12:
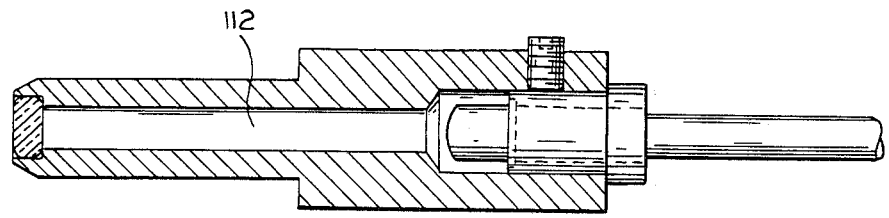
FIG. 12 is a side view of the radiant energy emitter associated with the level detector system in accordance with one embodiment of the present invention. The present invention taken along lines 12—12.

As shown in FIGS. 9 and 10, the container identifying means utilizes a bar code label 60 horizontally positioned on the lower portion 19 of the sample container by the clinician and a bar code sensor 62 located adjacent thereto for sensing the coded label. The bar code sensor 62 is a conventional reflectance-type radiant energy device capable of reading bar codes. It is preferred that the bar code sensor 62 remain stationary and that the sample container 16 be movable such that the entire code can be sensed. Therefore, the container is rotated about its vertical axis in front of the sensor 62 during reading of the bar code 60. A common occurrence in clinical laboratories, however, is the spillage of sample specimen along the side of the container or the placement of thumbprints on the sample container during handling. This can destroy a portion of the bar code 60 and can result in an inaccurate sensing of the bar code unless a broadened field of view is available to the sensor 62. In accordance with the present invention, the container is elevated as well as rotated during the reading of the bar code to permit the sensor to detect several regions of the code in a spiral fashion. Preferably, the sample container is rotated so as to make three revolutions about its vertical axis during this procedure.

The rotation of the sample container during sensing of the binary code 60 can be easily accomplished in a variety of ways. In accordance with the present invention, the rotation of the container is accomplished by the reversible engagement of a horizontally mounted clutch or rotating wheel 80 with the edge of the container as shown in FIG. 9. Circumscribed about the edge of the wheel 80 is a resilient bumper 82 made of rubber or the like for cushioning the contact between the wheel 80 and the container 16. The rotating wheel 80 is mounted adjacent to the transfer carousel 42 at a position coinciding with the sample identification position generally indicated at 84 and indicated by letter A in FIG. 5. The reversible engagement of the rotating wheel 60 with the container is controlled by the logic means of the analyzer.

Since the diameter of the sample containers varies from container to container, and some containers have irregular surfaces, rotation thereof during sensing of the bar code 60 can cause an error in the reflectance-measurement. The absolute requirement for error-free sensing of the bar code dictates that the focal length between the sensor 62 and the surface of the container remain constant. Consequently, the distance 64 between the bar code label 60 and the front edge 66 of the bar code sensor must not change in response to variations in container diameter or eccentric (out-of-phase) rotation.

In accordance with the present invention, the transfer carousel 42 is equipped with a means for maintaining the sensor 62 at a fixed distance from the surface of the sample container during rotation. One such means is shown in FIG. 9 and is illustrative of the type of mechanism which can be used in the present invention. The horizontally positioned sensor 62 is passed through an opening 67 in the vertical leg portion 63 of an L-shaped coupling member 65, and is securely coupled therethrough. The vertical leg 63 extends downwardly from the opening 67 and is connected to the top portion of a pair of spaced-apart vertical metal bar members 70 and 72 which are secured to each other at both ends by conventional nut and bolt 78 arrangements. The horizontal leg portion 76 of the L-shaped coupling member 65 has a small rotatable wheel 81 connected thereon. The wheel 81 is mounted on the base 74 through the vertical bars in a position to constantly engage an edge of the container during rotation, such that the distance 64 between the front edge 66 of the sensor and the edge of the container remains fixed. For example, if the diameter of the containers varies from one to another, or if the surface of a single container is irregular causes eccentric (out-of-phase) rotation, the sensor 62 is capable of maintaining its required degree of accuracy.

Although the sensor 62 can be connected to several different mechanisms as that described above for maintaining the fixed distance 64, we have found this embodiment provides an additional measure of accuracy in the bar code sensing procedure. As the sensor 62 is displaced laterally as shown by the arrows in FIG. 9, the upper portion of the spaced-apart vertical bars 70 and 72 traverses an arc as illustrated by the phantom lines. Consequently, the sensor 62 would have a tendency to be deflected upwardly out of its horizontal plane causing the light beam (not shown) to be deflected away from the binary code label 60. In accordance with the present invention, we have found that the bar code sensor 62 remains substantially perpendicular to the surface of the sample container at all times, and the light beam is not displaced vertically as the vertical bar members 70 and 72 are laterally displaced.

A significant contribution to the design of automated analytical analyzers in accordance with the present invention is that two or more types of sample containers can be employed. A first type of sample container is a conventional blood collection tube as described above for collecting blood samples from a patient. The second type of sample container, which has been specifically designed to hold small quantities of liquid is the subject of our copending application filed 7-20-81, Ser. No. 284,980, and has an elongated cylindrical housing of the same general shape as the conventional blood collection tube but has the sample holding compartment having smaller dimensions disposed at the top thereof. These micro-containers are easily handled by a laboratory technician, resulting in a rapid and reliable processing of fluid specimens for analysis.

Since the general dimensions overall of the micro-container are similar to the standard sample collection tube the clinician is able to conveniently grasp the micro-container by its elongated housing portion as he or she would a conventional container. This facilitates overall processing of the fluid samples since a clinician routinely handles a large number of tubes in a single day, and thus his efficient operation is not hampered by the manipulation of small, odd sized containers. The elongated housing also provides an adequate area for positioning of labels or other means of identification on the container to facilitate positive sample identification in an automated clinical analyzer. In addition, the elongated cylindrical housing acts as a permanent support for the micro-container such that tipping of the container and subsequent spillage of precious sample is avoided.

An important feature of the loading and transfer assembly of the present invention is its capability of introducing a patient's specimen into the analyzer from various sized containers. Although the micro-containers described above can easily be placed in the assembly, it is preferred to distinguish between the micro-containers and conventional containers for dispensing of the sample therefrom in order to avoid damage to the dispenser and to precisely position the dispenser during aspiration. Therefore, the assembly of the present invention includes a means of distinguishing between the two types of containers in the transfer carousel 42. Furthermore, the container distinguishing means can also be used in conjunction with the bar code sensor to determine the presence or absence of a container in the identification position 84 of the transfer carousel 42.

The identifying means in the preferred embodiment of the present invention includes a transmissive light source 86 and detector assembly 88 as shown in FIG. 10. The conventional light source 86 is a light-emitting diode which horizontally passes a beam of light through the sample container 16 to a light-detecting diode in the detector 88, unless the beam is blocked by the presence of a non-transparent label 90 or other indicia on the sample container. If no label 90 is detected during rotation of the container, the sample container is processed by the assembly as a micro-container. If a label 90 is detected, the presence of a conventional is confirmed. In order to establish whether or not a small volume container is truly present, a bar code 60 must be sensed as described above. If no label 90 or bar code 60 is sensed, the absence of any container in the transfer carousel 42 is confirmed and entered into the microprocessor assembly.

Figure 7:
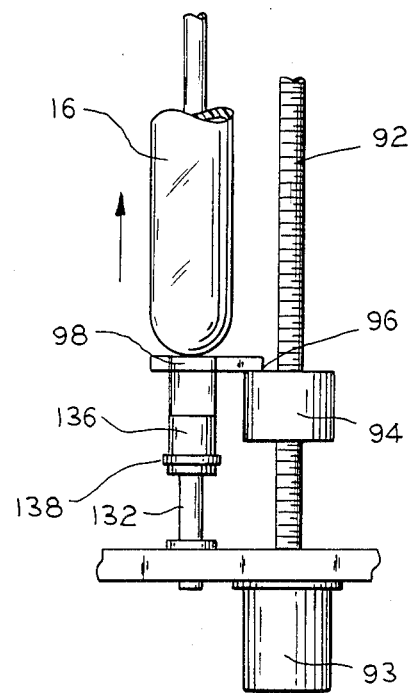
FIG. 7 is a side view of the means associated with said transfer carousel for elevating the containers in one embodiment of the present invention.

The elevation of the sample container during sensing of the bar code 60, as shown in FIG. 7 is accomplished by a conventional worm drive 92 connected to a gear and operated by a motor 93. A vertically moving nut 94 is freely mounted around the worm drive 94 as shown. Actuation of a motor causes rotation of the worm drive 92 with subsequent upward vertical movement of the nut 94. An edge portion 96 of the nut is positioned to engage the bottom portion of a sample container support 98 member as shown in FIG. 7. This causes the elevation of said support member 98 with consequent elevation of the container 16. The elevation means is further employed as part of a level-sensing device for accurately sensing the level of liquid sample in the containers. The level-sensing means and associated dispensing means are discussed in detail below.

Automated chemical analyzers employ various sample-dispensing means depending on the nature of the analysis system and the number of tests which can be conducted. These sample-dispensing arrangements have been devised to maximize the speed at which samples can be dispensed, and to mimimize contamination due to carry-over from adjacent samples. In accordance with the present invention, a means for dispensing the sample has been devised which is rapid, reproducible, and which eliminates sample carry-over. The main components of this system are a level-sensing means generally indicated at 110 in FIGS. 10-13, and a means associated with the dispensing mechanism for successively extracting sample from the containers in response to the liquid level therein. An additional advantage of the sample-dispensing means of the present invention is that sample specimens of different volumes can be analyzed without replacing the sample aspirator or predilution with reagents or diluents. The sample dispensing means of the present invention operates in a manner that advantagously permits the clinician to load specimens containers having different liquid volumes into the analyzer. The level-sensing means utilizes the worm drive container elevation system shown in FIG. 7 previously described to elevate the sample container.

Basically, the sample container is vertically raised until the meniscus of the liquid in the container reaches a predetermined level wherein the radiant energy from a radiant energy source 112 is reflected from the surface of the liquid to a radiant energy detector 114. The radiant energy emitter 116 and detector 114 are positioned relative to each other and to the sample container location such that the detector 114 will receive the reflected radiant energy at a threshhold value only when the meniscus reaches a predetermined level. Once this predetermined level has been reached, the vertical displacement of the sample container is stopped, and the sample container is subsequently maintained in the elevated position for further analysis.

Figure 6:
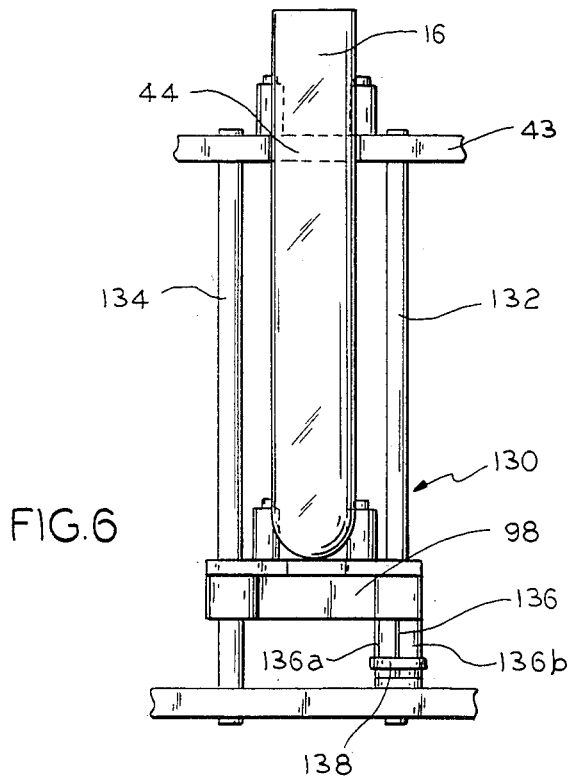
FIG. 6 is a side view of the means associated with the transfer carousel for retaining containers in accordance with one embodiment of the present invention.
Figure 8:
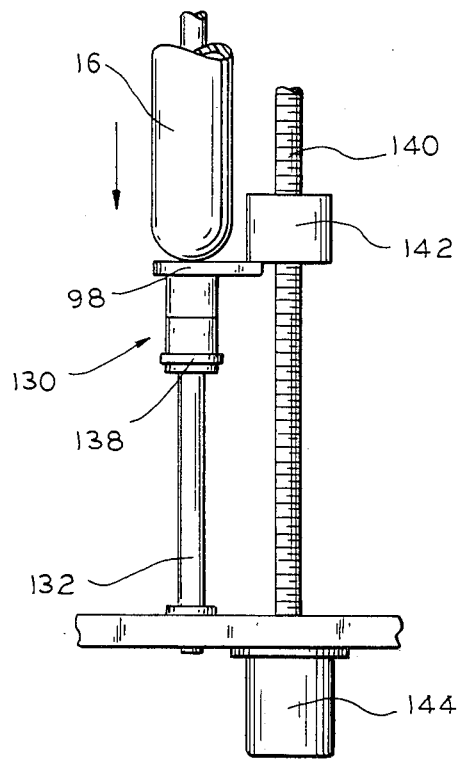
FIG. 8 is a side view of the means for lowering the containers in one embodiment of the present invention.

In accordance with the preferred embodiment of the present invention the elevation maintaining means generally shown at 130 in FIGS. 6 and 8 includes a pair of spaced apart vertical posts 132 and 134 mounted on the base of the transfer carousel 42. A horizontal base 98 for supporting the containers 16 is secured to the vertical posts 132 and 134 at its opposite end portions and is vertically movable at its opposite end portions and is vertically movable along the posts. Adjacent to and preferably connected to the horizontal base support 98 is a movable friction member 136 which is engageable with the base member 98 such that the friction member 136 will retain the base member 98 in an elevated position at any height along the vertical posts 132 and 134. Preferably the friction member 136a and 136b is constructed of two half-cylindrical sleeve members which are clamped together around the post 132 by a spring.

After dispensing of at least a portion of the sample from the container, the transfer carousel 42 can be rotated to position such that the horizontal base member 98 engages to a worm drive assembly 140 having the same general contruction as the elevation assembly. The only difference being that the nut 142 to position above the support member 98 such that the rotational movement of the worm drive 140 by motor 144 transmits a downward sample container to be removed from the transfer carousel at the some height that it was loaded.

In the preferred embodiment of the present invention, the radiant energy emitter 112 and radiant energy detector 114 are positioned on substantially opposite sides of a vertical plane defining the vertical axis of the sample container, and further positioned such that the emission of radiant energy is detected through reflectance from the air fluid surface of the sample on the container only when the meniscus reaches a predetermined level.

Figure 13:
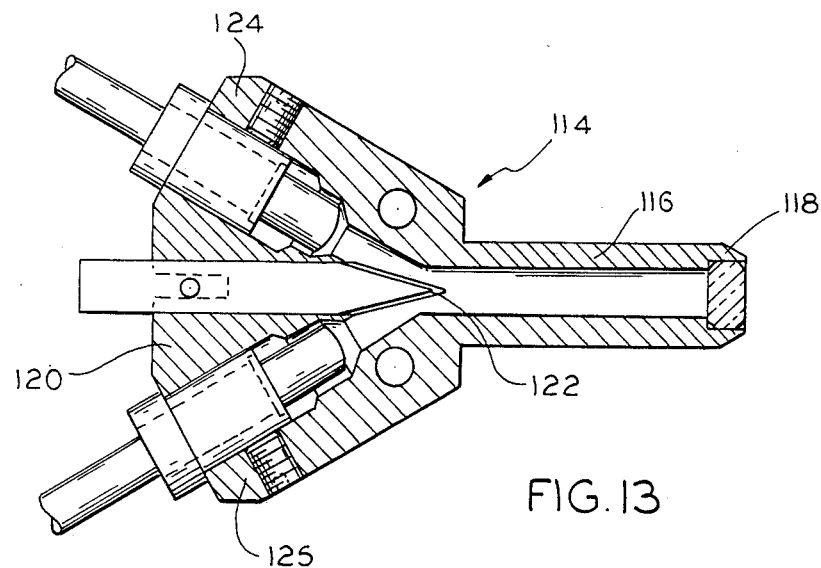
FIG. 13 is a side view of the radiant energy sensor associated with the level detector system of the present invention taken along lines 13—13.

As shown in FIGS. 10 and 13 the radiant energy detector 114 comprises a bifurcated housing 116 having a first housing member 118 aligned with the emitter 112 and a second housing member 120 extending on opposite sides of the first member 118; a means for sensing detected energy in each branch of the second member; and an energy-directing means positioned at the branch point of said housing to reflect radiant energy passing through the first housing 118 member to the energy sensors of the second member 120. The energy-directing means is preferably a bifrontal surface 122 such as a polished mirror which will deflect the radiant energy to either branch 124 or 125 of the detector housing. While a T-shaped bifurcated housing will suffice in accordance with the present invention, a Y-shaped housing is preferable.

An equivalent detector comprises a pair photocells positioned adjacent to each other detect the reflected energy, said photocells being positioned in close proximity to each other.

In accordance with the present invention is preferable to use infrared radiation as the radiant energy source however only radiation source capable of transmitting through the plastic or glass containers is suitable.

The transfer carousel of the preferred embodiment of the present invention further includes a container removing means as described hereinabove for the loading carousel, which removes the sample containers from the transfer carousel to a storage means for receiving the identified sample containers and retaining these sample containers in an organized manner.

Figure 14:
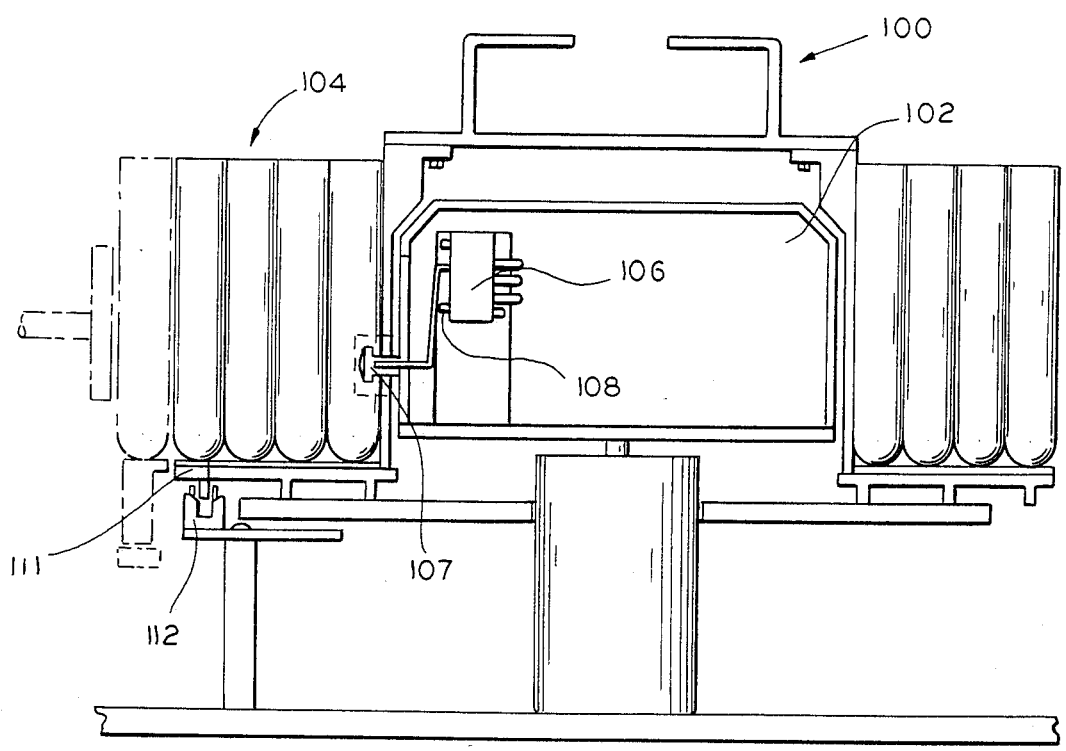
FIG. 14 is a front elevational view of a semi-circular storage carousel mounted in the assembly in accordance with one embodiment of the present invention.

The storage means of the present invention is preferably a rotating carousel 100 as shown in FIG. 14 having a substantially hollow inner core portion 102. The peripheral portion 104 of the carousel 100 has a plurality of radially extending slots (not shown) for receiving a number of conventional blood collection containers 16 as described for the loading carousel. The carousel 100 can be removably mounted in the assembly and thus allow the analyst to remove the positively identified for storage in a cold room or refrigerator. This collective storing capability is advantageous to the analyst becomes it reduces the error associated with the storage and transfer of individual containers. In the most preferred embodiment of the present invention, the storage carousel 100 is constructed of two semi-circular carousel portions, each portion having twelve radially extending slots large enough to fold four sample contaners each. The clinician thus has the capability of removing from the instrument without interrupting the processing therein. This allows the hospital clinician to efficiently conduct analyses on numerous samples and to provide test results on a continuous basis. In a preferred embodiment, the storage carousel 100 is interchangeable with the loading carousel 18 such that an empty storage carousel can be used immediately for collectively loading sample containers into the assembly 10.

Mounted on the interior 102 of the rotating storage carousel 100 is a means for indicating when the slot is full of containers. In the preferred embodiment, this is a sensor such as a microswitch 106 located adjacent the peripheral portion 104, which is activated as the sample containers are completely loaded in the radially extending slots as shown in FIG. 14. As the last container is unloaded from the transfer carousel 42, an actuating arm 107 is forced against a switch pin 108 and completes a circuit in the switching assembly 106. The activation causes the rotation of the storage carousel and positions an open slot in front of the exchange position 109(A) of the transfer carousel 42 for further unloading.

The storage carousel 100 further includes a means for locating sample containers and correlating this location with the positive identify of the sample container through a microprocessor after they have been removed from the transfer carousel 42. This facilitates the rapid location of sample and provides a backup system for the chemical anlyzer. For example, if an analysis of sample is inadequate or erroneous, or if the amount of a sample constituent is off-scale, the locating means of the storage carousel can be used to conveniently retrieve the sample for reloading in the loading carousel without further manipulation as in conventional analyzers. In conventional analyzers, any sample which must be repeated for the reasons discussed above must be reprocessed in order to obtain reliable test results. The preferred locating means associated with the storage carousel is a binary code 111 located on the bottom of the carousel which can be read by a binary code sensor.

PREFERRED OPERATION OF THE INVENTION

The overall operation of the loading and transfer assembly of the present invention is sequenced by a micro-processor system which delivers specific instructions to the various operating components of the assembly in response to the needs of the analyzer. These instructions correspond to specific test requests entered into the micro-processor terminal at the time a patient's sample is entered into the assembly by the analyst. Because the sample containers can be randomly loaded and positively identified in the assembly of the present invention, the test results are readily associated with the correct patient specimen with a minimum of the analyst's effort. Considerable time-consuming record-keeping tasks are significantly reduced, and errors in the reporting of test results is almost totally eliminated.

In a preferred embodiment of the present invention, a patient's blood or other biological fluid would be collected in accordance with a physician's instructions. If a blood sample is drawn from a patient, the phlebotomist draws the blood into a conventional blood collection tube or a specially designed micro-container as described in our co-pending application entitled *Container For Small Quantities Of Liquid*, Ser. No. 284,980, filed July 20, 1981. The phlebotomist then enters the patient's demographics and physicians's test requests into the microprocessor which generates a test list and identification corresponding to a bar code label and places the label on the blood collection tube. Hereinafter, no significant further manipulation or record-keeping is necessary before loading the specimen into the clinical analyzer.

Under normal circumstances, the coded specimen container is randomly loaded into a semi-circular carousel together with as many as 47 other containers. Two of these semi-circular assemblies 18, are mounted on the assembly by the analyst, rotates counterclockwise as it sequentially introduces sample containers into the exchange-slot position 46 of the transfer carousel 42. If the transfer carousel 42 is empty or only partially loaded with containers, the analyst may place the sample container directly therein. In an emergency or "stat" situation, a patient's specimen container is conveniently randomly loaded into one of several "stat" loading positions of the clockwise rotating transfer carousel at a position ahead of the preloaded containers in the assembly. There are essentially two types of "stat" loading positions in the preferred embodiment of the present invention.

The first type of "stat" loading position 48 consists of the container receiving slots located rearward of the container exchange slot position 46 which couples the loading and transfer carousel and forward of the container-exchange slot position which couples the transfer and storage carousels 109. Utilization of these "stat" loading positions permits the analyst to load containers into the assembly while maintaining the pre-loaded position of previously loaded containers in the entire assembly. Thus the analyst does not have to remove any containers from the assembly prior to entering a patient's sample into the type of "stat" loading position.

The second type of "stat"loading postion consists of a single container-receiving slot position 52 which is located forward of the container-exchange position 46 in the transfer assembly. Unless this slot position 52 is empty, a container must be removed by the analyst prior to loading the "stat" sample container. In accordance with the present invention, sample containers are randomly loaded into either the first 48 or second 52 type of "stat" positions since the means for positively identifying the containers 54 is positioned forward of both "stat" loading stations. This is a considerably advantage to the analyst since it eliminates the additional record-keeping associated with this type of exchange, and a considerable advantage to clinical analyzers in general since it reduces the chance of erroneously identifying the "stat" specimen.

During normal operation, the transfer carousel 42 rotates clockwise through a number of stations for performing operations on the patient's specimen. The time that a sample container remains in any one position in the rotational cycle of the carousel depends upon the number of analytical tests requested by the physician for that specimen, and is controlled by the microprocessor. The minimum rest time for a container in any one position is 10 seconds, since the microprocessor is either programmed to advance the carousel once during this interval, or contains instructions for only one test to be conducted on the specimen. On the other hand, at a rate of 5 seconds per test request, the rest time can be as great as 165 seconds if 32 analytical tests are requested.

In accordance with the present invention, the microprocessor sequences these various operations in the transfer carousel 42 in a more reliable and significantly more rapid manner than presently available automated clinical analyzers. Once the sample container is removed from the loading carousel 18, it is transported to the container-identifying location 54 which positively identifies the sample container and correlates it with the test requests entered by the analyst into the microprocessor. This is done by reading a bar code 60 placed on the container 16 by the phlebotomist. At about the same time, the transmissive-light source assembly 86 and 88 determines the presence or absence of a label 90 or other non-transparent portion on the sample container in order to distinguish between the conventional blood collection tubes and the micro-containers. In accordance with one embodiment the present invention, it is necessary for the microprocessor to know the type of the container, since the sample is dispensed from the containers at two different rates depending upon the cross-sectional area of the container holding the fluid.

The bar code 60 is read by a stationary binary code sensor 62 positioned adjacent to a sample container, which is positioned for rotation about its vertical axis. During sensing of the bar code, the container is also elevated such that the sensor senses the bar code along a spiral path to insure that no information is deleted. At about the same time, the transmissive-light source assembly 86 and 88 determines the presence or absence of a label 90 on the container or housing of the micro-container.

Once the sample container has been positively identified, the type of container determined, and the presence of a container confirmed, the assembly can dispense portions of the sample into the curvettes associated with the chemical analyzer. The first step is to elevate the container to a height that coincides with a predetermined height of the sample dispenser probe 146. In accordance with the present invention, the sample container is elevated by a worm drive assembly 92 and 94 until the meniscus of the fluid level is sensed by a level-sensing means such that precise sampling can be achieved by the dispensing means. If the dispensing means is not located at the elevating position, the container is maintained in the elevated position as the transfer carousel is rotated to the location of the dispensing means.

In accordance with the present invention, a fluid-sample dispensing probe 146 rotates to a position over the sample container, descends to the predetermined level where the lower portion of the probe's tip 148 intersects with the liquid surface, and aspirates sample therefrom. During aspiration of the sample, the probe tip 148 descends at a fixed rate depending upon the size of the container, such that the tip 148 of the probe 146 coincides with the meniscus level 150 of the fluid at all times. After transfer of the aspirated sample to a chemical analyzer, the probe returns to aspirate more sample if required, and descends to a new fluid level 152. The descent of the dispensor to the new fluid level and the rate of descent during aspiration are both controlled by the microprocessor.

With sampling completed, the transfer carousel rotates the sample container to a container lowering position which consists of a worm drive assembly 140 and 142. The lowering the container to its original height ocurrs before it is removed from the transfer carousel to the storage carousel 100. The container-exchange slot at position 109 associated with the storage carousel is equipped with a microswitch 106 which activates the rotational cycle of the storage carousel 100 when the slot is completely filled with sample containers. When actuated, the carousel rotates counterclockwise to make a new position available for unloading containers from the transfer carousel.

The storage carousel 100 is equipped with a binary code sensing system 111 for positively identifying the position of the sample containers in the storage carousel. Unlike the loading carousel 18 which contained randomly loaded containers, the storage carousel 100 carries the sample containers in a highly organized manner. As the containers are unloaded from the transfer carousel to the storage carousel, the binary code 111 associated with the slot position containing the unloaded container and the carousel number is sensed by the binary code sensor 112 assembly and the binary code number is printed out for the analyst whith the positively identified test results. The analyst can then retrieve the patient's specimen from a number of storage carousels simply by referring to the binary code number at the test result sheet.

Although the present invention has been described in terms of its preferred embodiments, and specific features have been set forth; it will be obvious to one having ordinary skilled in the art to make modifications and substitutions thereof without departing from the spirit and scope of the invention.

What is claimed is:

1. A transfer assembly in combination with a chemical analyzer for presenting a plurality of individual sample containers, having fluid samples therein, to the chemical analyzer which performs selected tests on the fluid samples, said assembly comprising:

first support means for supporting a plurality of individual sample containers for movement in a desired direction past a plurality of positions at which one or more operations are conducted on containers or the samples therein and signaling means associated with said support means for indicating whether said support means is in a moving or stationary mode of operation;

first means arranged adjacent said supporting means at a first position for automatically inserting individual sample containers into said supporting means and means associated with said support means for preventing the nongentle insertion of the individual sample containers into said support means, the first means comprising a second support means for receiving a plurality of individual sample containers in a random order and a container displacing means associated with said second support means to laterally displace containers from said second support means into said first support means responsive to the operation of the chemical analyzer;

second means arranged adjacent said first support means at a second position forward of said first position for identifying individual sample containers supported therein having means for sensing an information code on individual sample containers, said container displacing means randomly introducing individual sample containers into said support means at a position rearwards of said identifying means and forward or rearward of said automatic insertion means;

third means arranged at a third position forward of said second position for dispensing at least a portion of the fluid sample from each individual sample container, and further including means for positioning said dispensing means at a predetermined height, means for detecting the fluid sample level in the containers, and means for adjusting the height of individual sample container in response to said detection means so as to bring said fluid sample levels to a desired height in relation to said predetermined height;

fourth means associated with said support means for sequentially removing individual sample containers therefrom at a fourth position forward of said third position;

storage means for receiving individual sample containers removed from said support means at said fourth position, said storage means including means for identifying location of the individual fluid sample containers received therein; and means for controlling said transfer assembly to intermittently move individual sample containers past each of said first, second and third means and for controlling the operation of each of said first, second and third means whereby sample containers can be randomly inserted into said support means and wherein said control means further comprises a means for operating and selecting the test to be performed by said chemical analzyer in response to individual sample container identification obtained by said identifying means.

* * * * *